United States Patent [19]

Nobbio

[11] Patent Number: Plant 6,049

[45] Date of Patent: Dec. 1, 1987

[54] CARNATION NAMED "ELINOR"

[75] Inventor: Giacomo Nobbio, San Remo, Italy

[73] Assignee: Klemm & Sohn, Stuttgart, Fed. Rep. of Germany

[21] Appl. No.: 794,223

[22] Filed: Nov. 1, 1985

[51] Int. Cl.[4] ..... A01H 5/00

[52] U.S. Cl. ..... Plt./72

[58] Field of Search ..... Plt./72

*Primary Examiner*—Robert E. Bagwill

*Attorney, Agent, or Firm*—Charles W. Rummler

[57] ABSTRACT

A new variety of carnation having a closed calyx, characterized by its profuse and continuous year around production of deep pink flowers of medium size. This plant has a vigorous and upright growth habit with long, sturdy penduncles from 80 to 120 cm. long.

1 Drawing Figure

BACKGROUND OF THE NEW PLANT

This new carnation plant was developed during the course of breeding efforts carried on by me at San Remo, Italy since 1949 with the object of producing a sturdy carnation plant having a deep pink flower and a high production rate. The new plant originated as a seedling resulting from my crossing of selected varieties from breeding stock maintained at my greenhouse in San Remo, Italy, and was discovered in 1981 to possess the deep pink flower, sturdiness and cut-flower characteristics that I was seeking.

Asexual propagation of this new plant by cuttings has been carried out under my direction, at San Remo, Italy and many generations of such propagations have shown the novel characteristics of this plant to hold true and to be firmly fixed.

DESCRIPTION OF THE DRAWING

My new variety of carnation plant is illustrated by the accompanying full color photographic drawing, which shows a group of flowering stems having buds in various stages of opening, nearly opened flowers and blooms in further stages of maturity, the flower coloration being shown as nearly true as it is reasonably possible to obtain by means of conventional photographic procedures.

DESCRIPTION OF THE NEW PLANT

The following is a detailed description of my new carnation variety, based upon observation of the plants grown under conventional greenhouse practices, with color designations according to The R.H.S. Colour Chart, published by The Royal Horticultural Society at London, England.

THE PLANT

Origin: Seedling.

Parentage:

*Seed parent.*—Seedling No. 9,656 (unpatented).

*Pollen parent.*—Seedling No. 9,770 (unpatented).

Classification:

*Botanic.*—*Dyanthus caryophyllus.*

*Commercial.*—Greenhouse carnation for cut flowers.

Form: Bush height, about 1 to 1.10 m.

Growth: Vigorous and erect.

Branching: Normal.

Foliage:

*Quantity.*—Normal.

*Leaf size.*—Medium.

*Leaf shape.*—Very large and generally fan-shaped.

*Texture.*—Smooth.

*Color.*—Upper side — dark green. Under side — dark green.

THE BUD

Size: Medium, about 2.5 cm. to 3.0 cm. in diameter and about 2.5 cm. long.

Form: Ovoid.

Opening rate: Moderate.

Color:

*When sepals first divide.*—R.H.S. 62/B.

*When petals begin to unfurl.*—R.H.S. 62/B.

Calyx:

*Size.*—Large, funnel shape.

*Aspect.*—Smooth.

*Splitting.*—The Calyx does not split.

Sepals:

*Condition.*—Upstanding.

*Number.*—Five.

*Color.*—Inside — pale green; outside — dark green.

THE FLOWER

Blooming habit: Continuous and profuse.

Size of bloom: Medium, average diameter about 8–9 cm., depth about 2–2.5 cm.

Borne: Singly.

Shape: High center at first opening, and form does not change as the flower matures.

Petalage:

*Number of petals.*—About 80.

*Arrangement.*—Generally imbricated.

*Form.*—Fan shaped, with serrated and ruffled margins.

*Color.*—Outer and inside petals R.H.S. 62/B; reverse side R.H.S. 62/B.

*Texture.*—Soft.

*Appearance.*—Velvety.

Peduncle: Sturdy and upright.

*Length.*—About 80 to 120 cm.

*Color.*—Dark green.

*Strength.*—Medium.

Persistence: The flowers hang on and dry.

Fragrance: None.

Lasting quality: On the plant, good. As a cut flower, good.

REPRODUCTIVE ORGANS

Stamens: Absent in winter.
Pistils:
*Number.*—Three to four.
Styles:
*Length.*—About 2 cm.
*Color.*—White.
Stigmas:
*Color.*—White.
Ovaries: Ovoid.
Fruit: Fertile.
*Shape.*—Ovoid.
*Color.*—Green.

This new variety of carnation plant is particularly distinguished by the deep pink coloring of its flowers, which flowers are supported on a relatively long, sturdy peduncle. The flower has a closed calyx which does not split and the plant has an excellent capacity for continuous and profuse production of blooms, which is essential for the cut-flower market.

I claim:

1. A new and distinct variety of carnation plant, substantially as herein shown and described, characterized by its high productivity of deep pink flowers supported singly on a sturdy, upright peduncle, flowers being characterized by having a deep pink color.

* * * * *

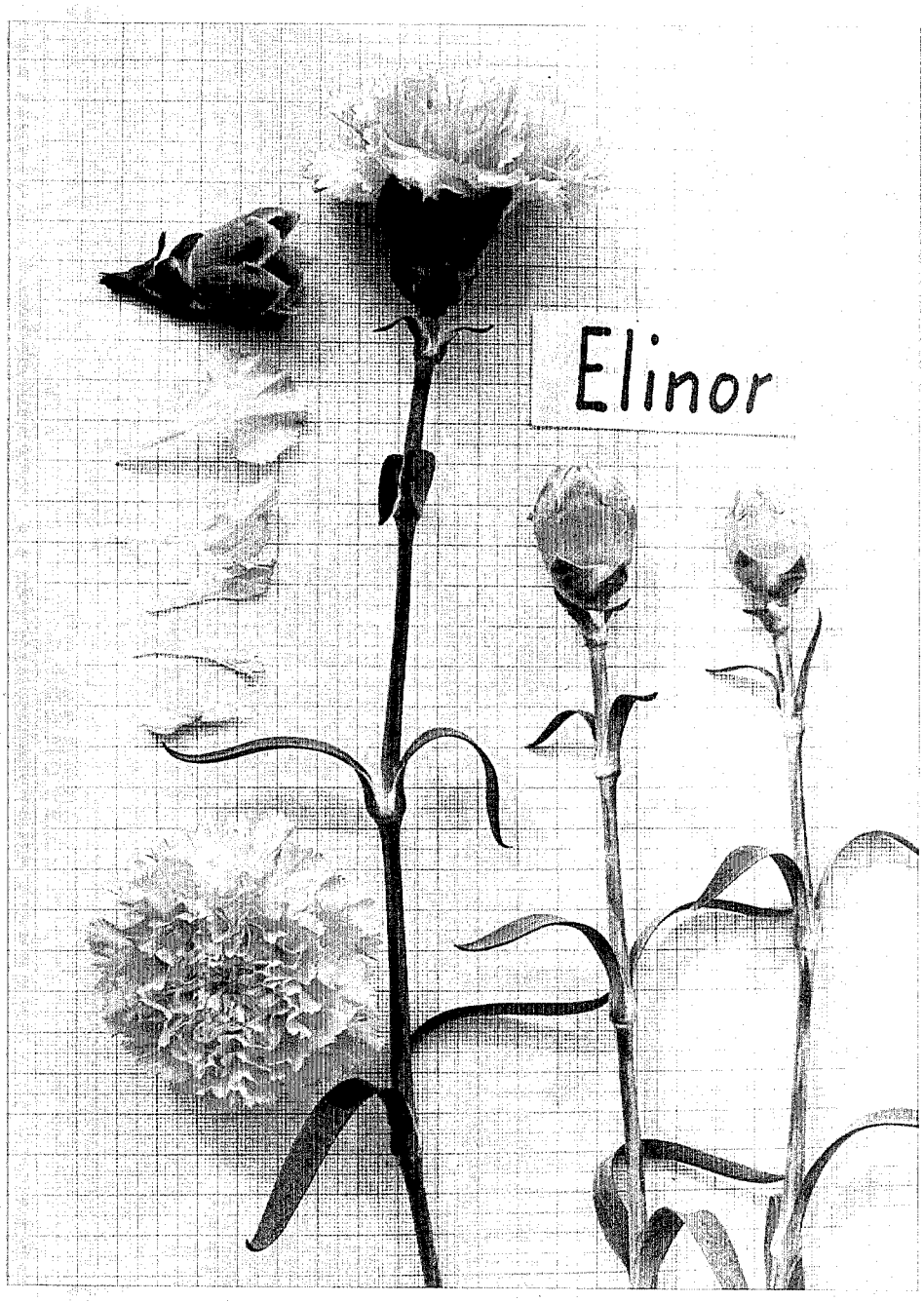
Elinor